United States Patent
Siess et al.

(10) Patent No.: US 8,123,669 B2
(45) Date of Patent: Feb. 28, 2012

(54) METHOD FOR CONTROLLING A BLOOD PUMP

(75) Inventors: Thorsten Siess, Wuerselen (DE); Rainer Damen, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 294 days.

(21) Appl. No.: 11/887,700

(22) PCT Filed: Apr. 13, 2006

(86) PCT No.: PCT/EP2006/061582
§ 371 (c)(1),
(2), (4) Date: Oct. 2, 2007

(87) PCT Pub. No.: WO2006/111503
PCT Pub. Date: Oct. 26, 2006

(65) Prior Publication Data
US 2009/0138080 A1    May 28, 2009

(30) Foreign Application Priority Data
Apr. 16, 2005  (DE) .......................... 10 2005 017 546

(51) Int. Cl.
*A61M 1/12*    (2006.01)

(52) U.S. Cl. ................ 600/16; 600/17; 607/17

(58) Field of Classification Search ............ 607/17; 600/16.17; 417/424.2, 20, 356
See application file for complete search history.

(56) References Cited

U.S. PATENT DOCUMENTS

| | | | | |
|---|---|---|---|---|
| 4,024,864 A | * | 5/1977 | Davies et al. | 604/67 |
| 4,781,716 A | * | 11/1988 | Richelsoph | 623/3.18 |
| 4,846,152 A | | 7/1989 | Wampler et al. | |
| 4,957,504 A | * | 9/1990 | Chardack | 623/3.14 |
| 5,290,227 A | * | 3/1994 | Pasque | 600/16 |
| 6,071,093 A | * | 6/2000 | Hart | 417/424.2 |
| 6,123,726 A | * | 9/2000 | Mori et al. | 623/3.27 |
| 6,139,487 A | | 10/2000 | Siess et al. | |

FOREIGN PATENT DOCUMENTS

| | | |
|---|---|---|
| EP | 0925080 B1 | 3/2004 |
| EP | 0961621 B1 | 7/2004 |
| WO | WO 03/105669 S | 12/2003 |
| WO | WO 2006/111503 | 10/2006 |

OTHER PUBLICATIONS

Hirofuni Anai, et al. "An Approach to Reducing Hemolysis in an Axial-Flow Blood Pump" Asaio Journal, Lippincott Williams Y Wilkins/ Asaio, Hagerstown, MD vol. 41, No. 3, Jul. 1, 1995, pp. 771-774.

* cited by examiner

*Primary Examiner* — Carl H Layno
*Assistant Examiner* — Pamela M Bays
(74) *Attorney, Agent, or Firm* — Fulwider Patton LLP

(57) ABSTRACT

A blood pump is temporarily operated at a low rotational speed lying below a design rotational speed. This involves a risk of thrombogenesis since flow detachments may occur at blades of an impeller of the rotary blood pump. For eliminating deposits at said impeller, the rotational speed of said pump is temporarily increased to the design rotational speed. Alternatively, said pump alternately operates at said design rotational speed and a low rotational speed, and this pulsed operation is synchronized with the heart rate.

8 Claims, 2 Drawing Sheets

METHOD FOR CONTROLLING A BLOOD PUMP

RELATED APPLICATIONS

This application is a U.S. national phase of PCT/EP06/061582, filed Apr. 13, 2006, which claims priority from German Application No. 102005017546.5, filed Apr. 16, 2005.

BACKGROUND OF THE INVENTION

The invention relates to a method for controlling the rotational speed of a rotary blood pump having a design rotational speed at which minimal detachment and swirling of the blood flow occur.

In EP 0 961 621 B1 (Impella) an intravascular blood pump is described which is inserted through the vascular system into the body and placed in the heart or at any other location where blood is intended to be pumped. The blood pump comprises a housing with a diameter of 5.4 to 6.4 mm which defines the stator of a motor. A rotor is connected with an impeller which rotates in a pump ring. This very small blood pump has a relatively high rotational speed in the range of 30,000 rpm.

In EP 0 925 080 B1 (Impella) a method for controlling a rotational speed of a blood pump is described, wherein the blood pump comprises pressure sensors for determining the pressure difference prevailing at the blood pump. The rotational speed of a motor is controlled in accordance with the signals supplied by the pressure sensors. Thus, a desired volume flow is generated which ensures the desired pumping action.

Continuously delivering rotary pumps have a so-called design rotational speed. The impeller advancing the blood is shaped such that at the design rotational speed flow detachments at the impeller blades are minimized, or, ideally, no flow detachments occur at all. Thus, a low-turbulent flow is obtained. Flow detachments and turbulences involve the risk of thrombogenesis, wherein blood accumulates and gathers at the impeller or at other locations in the blood system. This impairs the operation of the impeller. Further, this involves the risk of obstructions in the blood system.

SUMMARY OF THE INVENTION

It is an object of the invention to provide a method for controlling a rotational speed of a rotary blood pump, said method permanently ensuring highly efficient blood conveyance, and further allowing the blood pump to be temporarily operated below the design rotational speed.

The method according to the invention comprises the features of claim 1. Accordingly, the blood pump is operated at alternating rotational speeds, wherein the blood pump is operated alternately at a low rotational speed and at the design speed.

The invention is based on the fact that a thrombogenesis at the impeller can be prevented by at least temporarily operating the blood pump at the design rotational speed. However, it is also possible to operate the blood pump at a lower rotational speed without any risk involved. By increasing the rotational speed to the design rotational speed after a given operational period, a beginning thrombogenesis at the impeller is eliminated. It has turned out that a short-time operation at the design rotational speed is sufficient for removing blood clots from the impeller such that a buildup of blood clots is prevented. The invention allows for selecting a volume flow and/or delivery rate below the design rotational speed, and to vary said volume flow and/or delivery rate, if necessary, without a continuous operation at the high design rotational speed being required.

An increase from the low rotational speed to the design rotational speed is preferably performed at an acceleration of more than 3,000 $s^{-2}$. Thus, a rapid short-time increase in the rotational speed of the pump is attained. Such an increase is possible due to the small mass of the blood pump which is configured as an intravascular or paracardiac blood pump.

The rotational speed of the blood pump is preferably controlled by presetting an excitation frequency. The rotor is a slip-ringless direct current motor provided with cyclically excited coils in the stator and permanent magnets in the rotor. A controller arranged remotely from the rotor supplies an operating frequency for the motor. The motor is connected with the controller via an electrical conduit which extends through a flexible catheter.

The deceleration of the rotational speed requires a supply of energy. Said deceleration preferably takes place by a non-braked natural slowdown (damping performed by the driving impeller), wherein the deceleration also takes place within more than 3,000 $s^{-2}$ and thus within a very short time.

The invention allows the rotary blood pump to be operated according to a first variant of the inventive method, wherein pulses are periodically generated at the design rotational speed, and according to a second variant, wherein acceleration and deceleration are externally controlled.

In the first variant, the delivery rate is mainly determined by the low rotational speed, and the delivery volume is only marginally affected by the short-time increases to the design rotational speed. Consequently, the low rotational speed can be set according to a patient's need. When the heart of the patient has recovered due to the support provided by the blood pump and needs less support, a corresponding low rotational speed of the blood pump can be selected, wherein the thrombogenesis is prevented by short-time spike pulses which raise the rotational speed to the design rotational speed. These increases in the rotational speed only marginally affect the overall delivery rate of the blood pump.

In the second variant, the blood pump, which, in fact, is designed for continuous delivery, can be used for a pulsatile support of the heart. The pumping function of the blood pump is superimposed by the natural pumping function of the heart. This results in a periodically changing flow, wherein the periodic change is induced by the pumping function of the heart which temporarily supports the action of the blood pump, namely during the systole, and temporarily restrains the action of the blood pump, namely during the diastole. The invention allows, by monitoring of the motor current, the periods of high rotational speeds of the pump and the periods of low rotational speeds of the pump to be synchronized with the pumping function of the heart, and/or to be triggered in an out-of-phase relationship to the heart function without an ECG lead being required.

BRIEF DESCRIPTION OF THE DRAWINGS

The invention is in particular suitable for right ventricular support, where the intake opening of the pump is placed in the right atrium, while the pump delivers into the pulmonary artery.

Embodiments of the invention will now be described in greater detail with reference to the drawings in which.

DETAILED DESCRIPTION

Figure 1:
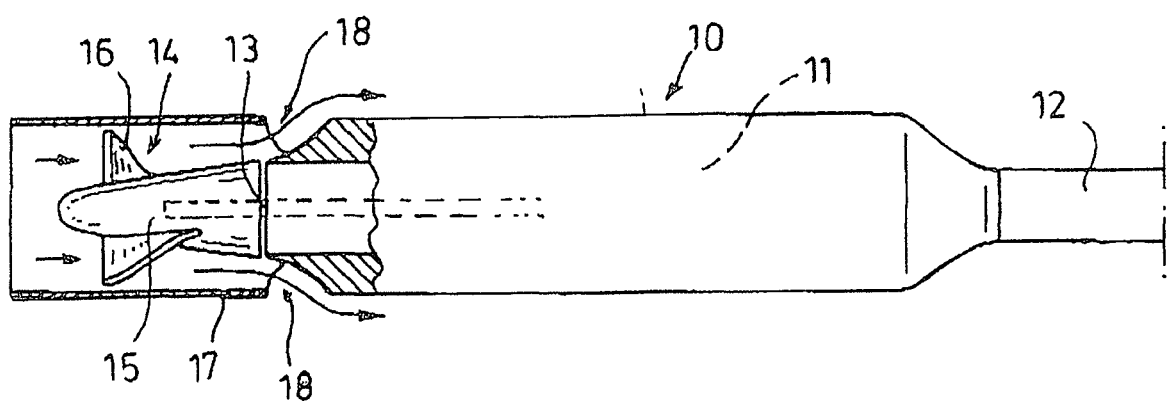
FIG. 1 shows a schematic representation of the configuration of the blood pump.

FIG. 1 shows a rotary blood pump 10 for supporting the heart function. Here, the blood pump is an intravascular pump whose maximum outer diameter is at no place larger than 7 mm. The blood pump may also be configured as an intracardiac blood pump which is inserted through an incision of the heart. Such a blood pump may have a somewhat larger diameter. Further, the pump may be placed paracardiacally (around the heart) and take blood via two incisions from a location in front of the heart or from the heart, and return the blood via the second incision behind the heart.

The blood pump 10 comprises an elongate cylindrical motor 11 whose proximal end has connected therewith a flexible catheter 12. Electrical conduits (not shown) extend through the catheter 12 to a controller.

A shaft 13 of the motor 11 carries an impeller 14 with a hub 15 tapering towards a distal end thereof, with helical blades 16 extending from said hub 15.

The impeller 14 is surrounded by an elongate ring 17 which has approximately the same outer diameter as the motor 11. Between the motor 11 and the ring 17 outflow openings 18 are arranged. When rotating, the impeller 14 axially takes in blood and conveys the blood towards the motor 11. The blood leaves the blood pump through the openings 18 so as to subsequently flow along the motor 11. The pump shown in FIG. 1 may further have a fluidic design which allows a reverse direction of flow to be obtained.

Figure 2:
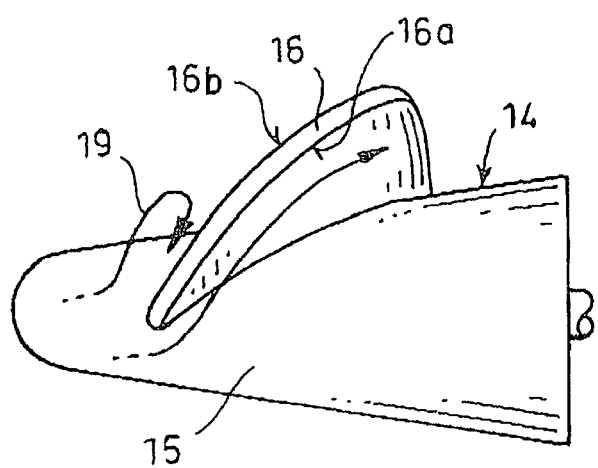
FIG. 2 shows, on an enlarged scale, the flow conditions at a blade of the pump impeller.

FIG. 2 shows a schematic enlarged representation of a portion of the impeller 14. A blade 16 extends from the hub 15, said blade 16 being bent like a wing of an aircraft. The flow generates a positive pressure at the concave inside 16a, and a vacuum or negative pressure is generated along the convex upper side 16b. The blades 16 are configured such that at a design rotational speed a detachment-free flow along the blades is obtained. In the present embodiment, the design rotational speed is 30,000 rpm. At lower rotational speeds flow detachments and swirls 19 occur which may damage the blood due to thrombogenesis. Blood clots grow on the surface of the blade 16 and affect the blood flow, thereby promoting the thrombogenesis.

Figure 3:
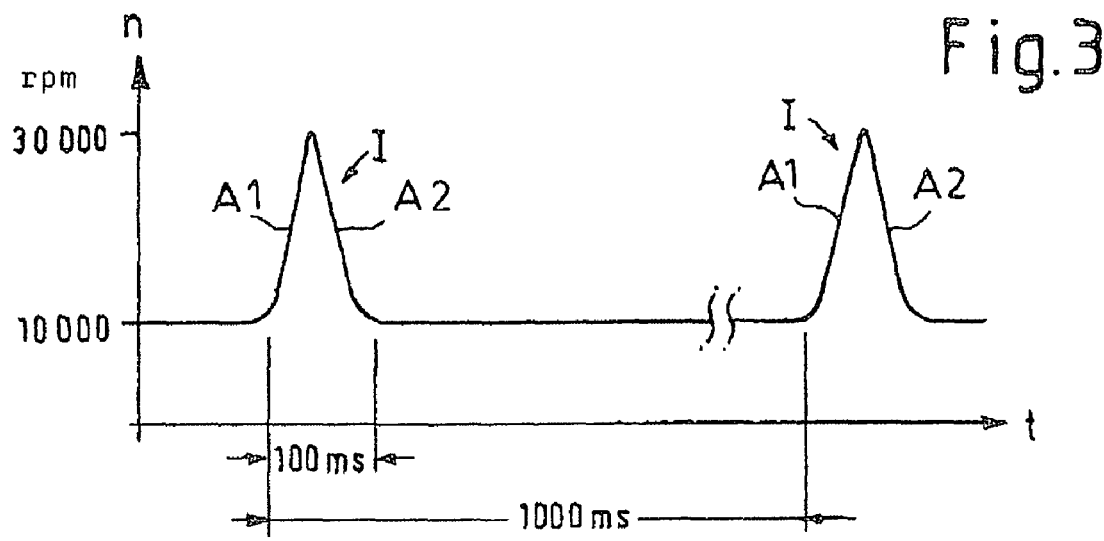
FIG. 3 shows the time profile of the pump rotational speed at periodic control.

FIG. 3 shows a diagram of a time profile of the rotational speed n of the motor 11, wherein along the abscissa the time t is plotted, and along the ordinate the rotational speed n per minute is plotted. The rotational speed can be varied by correspondingly adjusting the controller. In the present embodiment it is assumed that the rotational speed generally is 10,000 rpm. This value exemplifies a delivery rate required by a patient for supporting the heart function during a recovery phase.

The continuous rotational speed of 10,000 rpm is interrupted by periodically generated pulses I, wherein during the pulse duration the rotational speed temporarily increases to the design rotational speed of 30,000 rpm. The rising edge A1 of the pulse I has a slope of more than 3,000 $s^{-2}$. Here, the rotational speed of the motor continuously increases from the low value of 10,000 rpm to the design rotational speed of 30,000 rpm. This rise in frequency is produced by the controller. When the design rotational speed has been reached, the rotational speed slows down in a trailing edge A2. Said slowdown takes place without supply of braking energy or any other external energy just by non-supply of driving energy. The slowdown, too, takes place with a delay of more than 3,000 $s^{-2}$. The slowdown is terminated when the rotational speed has returned to the lower value which is subsequently maintained. In the present embodiment, the duration of the pulse I is approximately 100 ms, and the pulse cycle time, i.e. the duration of a pulse and a subsequent interpulse period, is approximately 1,000 ms.

The pulses I are spike pulses with a small pulse width relative to the pulse cycle time. Therefore, the additional delivery rate produced by the pulses I is small relative to the basic delivery rate at 10,000 rpm. Thus, the pulses I influence said basic delivery rate only to a small extent. The pulses I have the effect that despite a small flow thrombogenesis at the impeller is prevented even over a period of several days.

Figure 4:
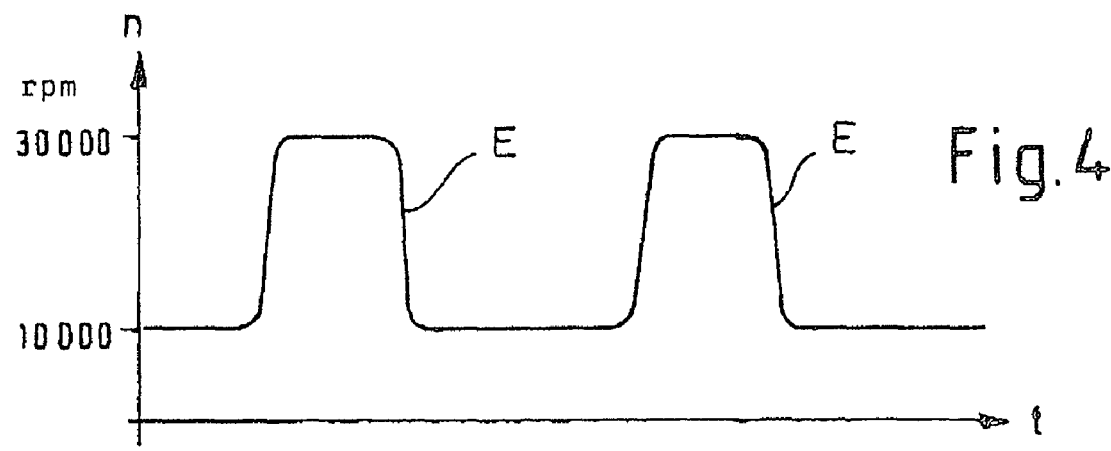
FIG. 4 shows the time profile of the pump rotational speed at a pump operation synchronized with the heart function.
Figure 5:
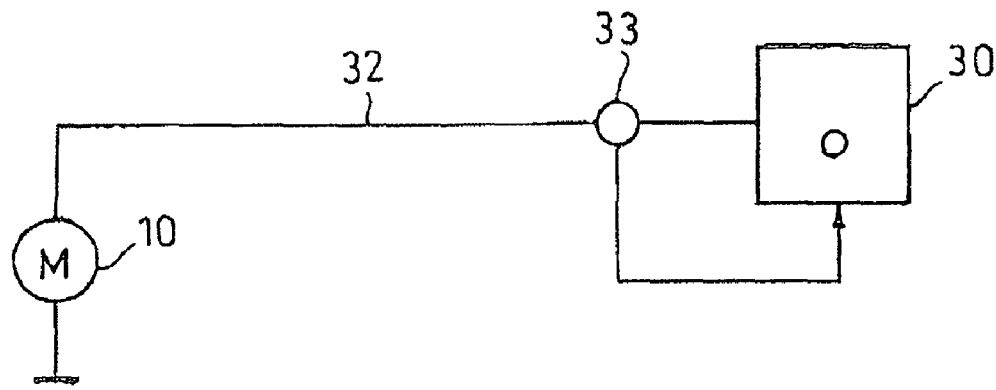
FIG. 5 shows a schematic representation of the pump drive unit and the sensor for determining the motor current.

FIG. 4 shows a second variant of the method according to the invention. In this variant, too, the rotational speed n is temporarily increased by pulses E, but said pulses E are substantially wider than the pulses I of the first method variant. The pulses E, during whose duration the rotational speed is temporarily increased, are produced synchronously with the heart rate, but out of phase relative thereto. FIG. 5 shows the circuitry of the motor 11 and a controller 30 which supplies the frequency and the current for the motor 11. The controller 30 is connected with the motor via a conduit 32. A sensor 33 measures the current flowing in the conduit 32 and communicates the respective value to the controller 30. The motor current depends on a load of the motor. The load changes over time in accordance with the natural pumping action of the heart which is superimposed on the continuous pumping action of the pump 10. From the time profile of the current measured by the sensor 33 the timing for the generation of the pulses E of FIG. 4 can be derived. Thus, an ECG lead comprising additional measuring electrodes is not needed. The pump does not require any external sensors.

As shown in FIG. 4, in this variant, too, the pump is operated such that either a low rotational speed n or the design rotational speed is set. Here, too, the acceleration of the pump and the deceleration take place within more than 3,000 $s^{-2}$. In this pump operation variant, the rotary blood pump generates a pulsating pump operation which is attuned to the natural pumping frequency of the heart.

The invention claimed is:

1. A method of operating a rotary blood pump comprising:
    providing a rotary blood pump having an impeller shaped such that blood flow over said impeller is detachment free and swirl free at an elevated rotational speed of at least 30,000 rpm to thereby eliminate thrombogenesis on said impeller;
    operating said pump at a lower rotational speed of about 10,000 rpm at which speed thrombogenesis may occur; and
    intermittently operating said pump at said elevated rotational speed to eliminate any such thrombogenesis on said impeller.

2. The method according to claim 1, wherein the rotational speed of the blood pump is increased from its lower rotational speed to said elevated rotational speed at a rate of acceleration of more than 3,000 $s^{-2}$.

3. The method according to claim 1, wherein the rotational speed of the blood pump is decelerated from said elevated rotational speed to said lower rotational speed by a natural slowdown without supply of braking energy.

4. The method according to claim 3, wherein the rate of deceleration exceeds 3,000 $s^{-2}$.

5. The method according to claim 1, wherein intermittent operation of said blood pump at said elevated rotational speed defines periodic pulses (I) with a pulse period at least five times longer than a width of the pulse (I).

6. The method according to claim 1, wherein the blood pump is driven by an electric motor drawing a current in order to maintain a preselected operating frequency, further comprising measuring said current, determining from any variation thereof a frequency of a superimposed pumping, and synchronizing the operation of the blood pump with the superimposed pumping function.

7. An intracardiac blood pump comprising an electric motor connected to a controller via a catheter, and an impeller driven by said motor, wherein said impeller is shaped such that while thrombogenesis may occur at a lower rotational speed of about 10,000 rpm, blood flow over said impeller is detachment free and swirl free at an elevated rotational speed of at least 30,000 rpm at which thrombogenesis forming on said impeller is eliminated, wherein said controller varies a rotational speed of said pump between said elevated rotational speed and said lower rotational speed.

8. The intracardiac blood pump of claim 7, further comprising a sensor for measuring current drawn by said electric motor, wherein said electric motor draws a current in order to maintain a preselected operating frequency and the controller varies the rotational speed of said pump between the elevated rotational speed and the lower rotational speed as a function of signals supplied by said sensor.

* * * * *